United States Patent

Weintraub

[11] Patent Number: 4,831,066
[45] Date of Patent: May 16, 1989

[54] DENTAL COMPOSITIONS COMPRISING OLIGOMER OF HEXAHYDROPHTALIC ANHYDRIDE, GLYCIDYLMETHACRYLATE AND 2-HYDROXYETHYL-METHACRYLATE

[75] Inventor: Yuri Weintraub, Forest Hills, N.Y.

[73] Assignee: IPCO Corporation, White Plaines, N.Y.

[21] Appl. No.: 81,646

[22] Filed: Aug. 4, 1987

[51] Int. Cl.$^4$ ............................................... C08J 2/00
[52] U.S. Cl. ................................... 523/116; 523/115; 523/117; 523/118
[58] Field of Search ............... 523/115, 116, 117, 118; 560/127

[56] References Cited

U.S. PATENT DOCUMENTS 4,420,306 12/1983 Orlowski et al. .................... 523/117

Primary Examiner—Joseph L. Schofer
Assistant Examiner—Peter D. Mulcahy
Attorney, Agent, or Firm—Helfgott & Karas

[57] ABSTRACT

Dental restorative compositions comprising a polymerizable poly functional methacylate having the chemical structure:

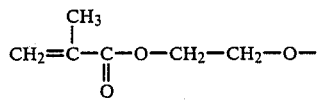
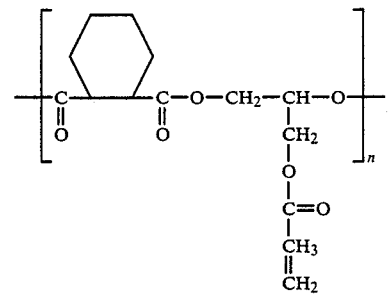
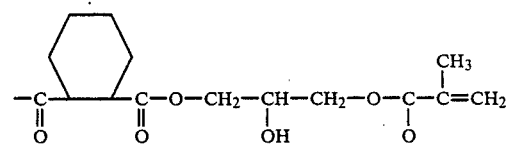

wherein n=1–3, and a filler are disclosed, the binder oligomer and polymer formed are also taught.

5 Claims, No Drawings

DENTAL COMPOSITIONS COMPRISING OLIGOMER OF HEXAHYDROPHTALIC ANHYDRIDE, GLYCIDYLMETHACRYLATE AND 2-HYDROXYETHYL-METHACRYLATE

FIELD OF THE INVENTION

The present invention relates to the use of polymerizable polyfunctional methacrylates having the following chemical structure:

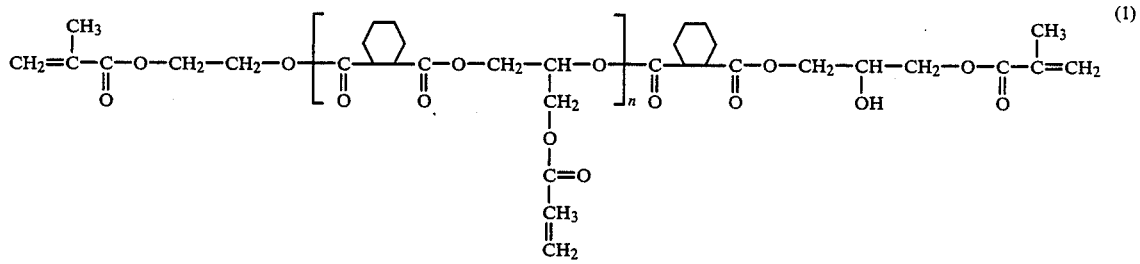

HHPhA—GMA Oligomer (Hexahydrophtalic anhydride glycidylmethacrylate oligomer)

wherein n=1-3, and dental compositions comprising these methacrylates.

BACKGROUND OF THE INVENTION

In recent years the use of polymer based dental materials has gained in prominence, since these materials have improved physical and mechanical properties and provide dental restorations having superior durability. These materials have been found to be particularly useful as filled restorative materials, bonding agents, tissue scalers and orthodontic adhesives, particularly those materials, based upon polymerizable aromatic and aliphatic methacrylates, which polymerize in situ, most with the application of visual light.

The best properties in these types of materials have been obtained when the resin part of the composition is comprised of one or more of the following monomers:

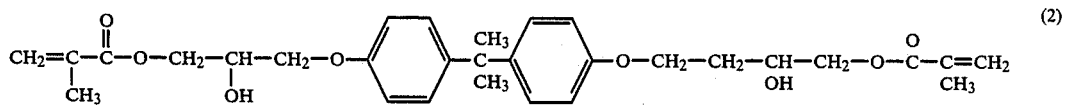

2,2-bis[4'-(3"-methacroyl-2"-hydroxypropoxy)-phenyl]-propane, known in industry as BIS-GMA, its adduct with various alkyl, iso, or diisocyanates, such as the adduct described by Waller, U.S. Pat. No. 3,629,187 and urethane dimethacrylates as are described, for example, in the U.S. Pat. Nos. 3,425,988; 3,709,866 and 3,629,187, and the like.

These products have a high molecular weight and viscosity and must be used in compositions with dilutants of low viscosity methacrylates, such as di- or tetra-ethylenglycol dimethacrylates, 1,6-hexandiol dimethacrylate or trimethylolpropane trimethacrylate. Most of these prepolymer type of monomers have a diphenylolpropane base. They possess in their molecular structure an aromatic double cycle and a strong ability to absorb curing light which makes deep curing difficult. The two hydroxyl groups in the molecule of BIS-GMA, which has a molecular weight of 512, make both the viscosity of the monomer and water absorption of the composition high. Synthesis of this pure monomer is also quite difficult.

In an attempt to improve methacrylate resin based dental materials, research efforts have been concentrated mainly on reducing their water absorption characteristics, minimizing their polymerization shrinkage and on improving their resistance to discoloration when exposed to sunlight. All of these properties depend upon the chemical structure of the monomer or monomers used in the formulation as well as their purity.

These research efforts have produced new formulations in the last few years, such as, for example, adducts of 3-methacroyl-2-hydroxypropylesters with diisocyanates of Orlowsky et al. U.S. Pat. No. 4,490,115. The efforts of Bowen to obtain methacrylate monomers with branched poly functional structure based on adduct of hydroxyethyl methacrylate and pyromellitic dianhydrid have permitted the creation of materials with improved adhesion to dentine and enamel. Industrial and Engineering Chemical Product Research and Development, pg 78–81 March 1984.

In addition to various aforementioned references polymeric dental materials have been described in the following U.S. Pat. Nos.: 3,066,112 (Bowen); 3,179,623 (Bowen); 3,194,783 (Bowen); 3,194,784 (Bowen); 3,539,533 (Lee II et al.); 3,541,068 (Taylor); 3,597,389 (Taylor); 3,721,644 (Stoffey et al.); 3,730,947 (Stoffey et al.); 3,751,399 (Lee Jr. et al.); 3,766,132 (Lee Jr. et al.); 3,774,305 (Stoffey et al.); 3,860,556 (Taylor); 3,862,920 (Foster et al.); 3,926,906 (Lee II et al.); 4,102,856 (Lee Jr.); 4,107,845 (Lee Jr. et al.); 4,490,115 (Orlowsky et al.); 4,544,359 (Waknine); 4,536,523 (Antonucci); 4,551,486 (Tateosian); 4,552,906 (Podszun); 4,553,940 (Koblitz et al.).

SUMMARY OF THE INVENTION

The present invention relates to an oligomer, obtained on the base of hexahydrophtalic anhydride of the following formula, or any aromatic and aliphatic anhydride thereof, such as, for example tetrahydrophtalic, or phtalic.

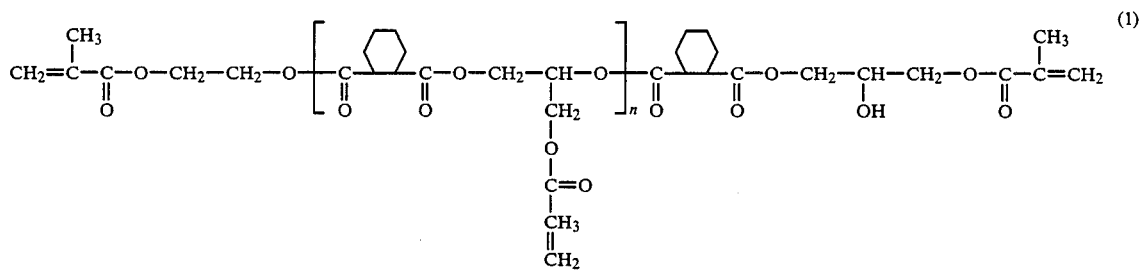

HHPhA—GMA Oligomer (Hexahydrophtalic anhydride glycidylmethacrylate oligomer)

This invention also relates to the polymer formed from this oligomer and to dental materials, in particular composite restorative materials containing this oligomer.

DETAILED DESCRIPTION OF THE INVENTION

This invention relates to polyfunctional methacrylate compounds represented by the oligomer structure (1). Oligomers of this formula are referred to herein as compound of the present invention.

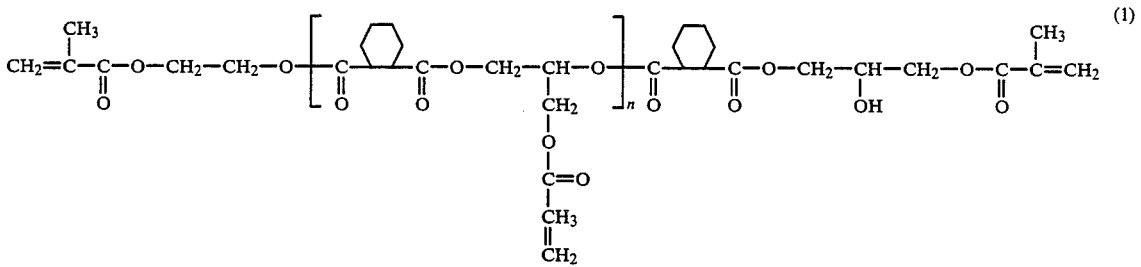

HHPhA—GMA olygmer

The reaction for obtaining this oligomer is carried using a tricomponent mixture where the correlation between the amount of each of the components taken for reaction determines the degree of oligomerization "n" and the molecular weight of the final oligomer. The first two components: hexahydrophtalic anhydride and glycidyl methacrylate must be taken in equimolecular amounts. The molecular quantity of the third component 2-hydroxy ethyl methacrylate regulates the molecular weight of the final product. For example: the reaction of 2 moles each of the two first components and one mole of the third component results in an oligomer with a degree of oligomerization n=1 and with M.W. 722. Further, 2:5 moles of the first two components and one mole of the third component produce an oligomer which is 50:50 mixture of di- and trimer with average MW=870. Oligomers with a degree of oligomerization more than 3 have been found to be unsuitable for use in dental compositions because of their high viscosity, but oligomers with n=1–3 showed excellent results for use as dental compositions.

The advantages of the oligomers of the present invention derive from their polyfunctional branched structure, relatively high molecular weight with low viscosity, absence of aromatic structure, clearness, the presence of only one hydroxyl group per molecule, and the ease of synthesis of the pure product.

The reaction to produce the oligomers of the present invention may take place in the presence of a suitable electron donating catalyst such as a tertiary amine or tertiary alkoxy amine and a polymerization inhibitor, such as for example butylated hydroxytoluene, or hydroxyquinone. The reaction is carried out in nitrogen atmosphere with a small increase in temperature prior to the end of the preparation.

A composite restorative material is a composite material comprising a polymerization material and a suitable filler. These materials must be capable of curing in situ on teeth to restore a hardened surface thereto. These materials are generally applied as a filling material to prepared or drilled teeth.

Accordingly, composite restorative materials should have a thick, workable consistency suitable for application to a prepared tooth and capable of being shaped or molded thereon before setting occurs. Particularly preferred inorganic filler materials include silica materials (e.g. powered quartz, barium glasses, borsilica, and strontium silica glasses, $SiO_2$, fumed silica, precipitate and colloidal silica).

There are commercially available a few types of composite material which depend upon the type of filler used in the compositions. These include large particle composites (size of particles 15–30 mk), microfill composites (size of particles 0.04 mk), fine particle composites (size of particles 1–8 mk), blended composites (size of particles 0.04–5.0 mk)

The amount of filler depends upon the type of composition and may vary from 51–53% by weight for microfill composites and up to 79% by weight or more for other type of composites.

EXAMPLES

While the invention has been described above, the details of the present invention will be better understood by recourse to the following examples:

EXAMPLE I 32.8 gr hexahydrophtalic anhydride, 28.4 gr glycidil methacrylate and 13.0 gr of 2-hydroxyethyl methacrylate were placed in three throat flask, provided with a condenser and an agitator. Reaction was carried out in the presence of 0.4 gr. of N,N-diethylethanol amine as a catalyst and 0.025 gr of hydroquinone as an inhibitor. The reaction mixture was kept at a temperature 85° C. in a nitrogen atmosphere with good mixing. After 4 hours the temperature was raised to 95° and the reaction mixture maintained at this temperature for 1.5 hours. The residue is a colorless liquid of significantly less viscosity than BIS-GMA (Viscosity of obtained oligomer with M.W. 722 is 2500–2800 cps at 25° C.).

EXAMPLE II 41.0 gr of hexahydrophtalic anhydride, 35.5 gr. of glycidyl methacrylate and 13.0 gr of 2-hydroxyethyl methacrylate were taken for reaction. The reaction mixture has kept at a temperature 85° C. for 4 hours and then the temperature was raised to 95° C. for 1.5 hours more. The obtained product was a 50:50 mixture of the oligomers with n−1 and n=2, with average M.W. 870, and was a viscous, colorless liquid of significantly less viscosity than BIS-GMA.

The polymethacrylate of the present invention may be combined with other polymerizable unsaturated materials such as, acrylic, methacrylic monomers and then polymerized. They are recommended for use in dental compositions with dilutants, low viscosity methacrylates like di- or triethylene glycol dimethacrylates, hexamethylenglycol dimethacrylate and the like in proportions from about 1:1 to 2:1 and more.

Polymerization of the polymethacrylates of the present invention may be initiated by a variety of know means such as heat, chemical means or photo chemical initiations. Thus, in order to induce curing of polymethacrylates a free-radical catalyst may be incorporated therein. Organic peroxide initiators such as methyl ethyl ketone peroxide t-butyl peroctoat, isopropyl percarbonate, cumene hydroperoxide, dicumyl peroxide, and especially benzoyl peroxide are preferred. The ability of the initiator to cure polymethacrylates may be enhanced through the use of activators or accelerators such as tertiary aromatic anines N,N-dimethyl-p-toluidine or N,N-bis(2 hydroxyethyl)-p-toluidine. The amount of catalyst depends upon the needed curing rate and may be selected from 0.4% to about 4.0% by weight of the polymerizable components. As with the free radical catalyst, the amount of the activator selected may vary from about 0.4 to about 0.4% by weight of the polymerizable components, depending upon the desired curing rate.

Polymerization of the polymethacrylates of the present invention may also be initiated by ultraviolet or visible light, using known light activated polymerization initiators such as DL Camphorquinone, benzoin, benzil, and the like, as well as the above photo-initiators used with activators such as tertiary aliphatic or aromatic amines like N,N,N,N,-tetramethylenediamine (TEMED) or dimethylaminoethyl methacrylate (Ageflax-FM-1).

The amount of initiator, preferably 0.08–0.24% and of activator, 0.1–0.5% by weight of the polymerizable components, depend upon the thickness of sample and the desired curing rate. The amount of tertiary amine used as a catalyst in the main reaction and left in the monomer may be calculated.

EXAMPLE III

A polymer matrix of the composition of the present invention was prepared by diluting polymethacrylic monomers in triethyleneglycoldimethacrylate in weight ratio range of from about 2.0:1 to 1:1.

The polymer matrix was prepared for a light curing process contained 0.15% wt of camphorquinone as a photoinitiator and 0.5% wt. of dimethylaminoethylmethacrylate as an activator of polymerization and 0.05% wt 2,6-di-tert-butyl-4-methylphenol as an inhibitor.

Radiopaque dental filler strontium silica glass-type IX-2405 "R", having a particle size of 7–22 mk, produced by Innotech Glass Division Co., was used in the composition of the present invention as a filler after preliminary silanization with 3-methacryloxypropyltrimethoxy silane of Dow Corning Z-6030. Specimens of cured composites containing monomers according to the present invention exhibited desirable properties and were capable of holding up under strong mastication forces.

EXAMPLE IV

A typical formulation of a dental filler composition was prepared according to Example III having the following composition:

| | |
|---|---|
| Oligomer n = 1.0 | 21.55% wt. |
| Triethylenglycol dimethacrylate | 10.8% wt. |
| Radiopaque strontium silica glass IX-2405R | 77.0% wt. |
| DL-Camphorquinone | 0.15% wt. |
| Dimethylaminoethyl methacrylate Ageflax FM-1 | 0.5% wt. |

Various samples of composite material were examined after curing with light and demonstrated the following properties:

| | |
|---|---|
| Hardness Barcol | 96-98 (3.5 mm thickness of specimens) |
| Water absorbtion | 0.15 mg/cm2 |
| Polymerization shrinkage, linear | 0.2–0.4% |

These results are well within the standards as set out in Specification N27 of ADA.

All of the characteristics of the composition of the present invention indicate a high degree of utility as a dental restorative material.

While the invention has been described with respect to various specific examples and embodiments, it is to be understood that the invention is not limited thereto and that it can be variously practiced within the scope of the following claims.

I claim:

1. A dental restorative composition comprising a polymerizable polyfunctional methacrylate of the formula

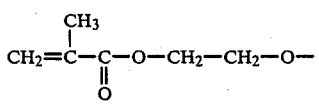

-continued

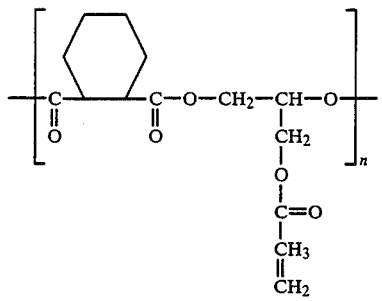

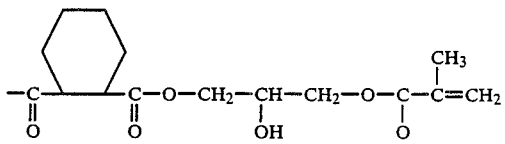

wherein n=1-3 and an inorganic filler selected from the group consisting of fused silica, silica glass and crystalline quartz.

2. A dental restorative composition according to claim 1, which also comprises one or more additives for the initiation of the polymerization thereof.

3. A dental restorative composition according to claim 2, which also comprises one or more additives for the inhibition of the polymerization thereof.

4. The composition of claim 1, in combination with a material suitable as dental filler material.

5. The composition of claim 1 in combination with a material suitable as a dental filler and a polymerization initiator.

* * * * *